(12) United States Patent  (10) Patent No.: US 9,134,226 B2
Nicoletti et al.  (45) Date of Patent: Sep. 15, 2015

(54) OPTICAL GAS DETECTOR

(71) Applicant: Commissariat a l'Energie Atomique et aux Energies Alternatives, Paris (FR)

(72) Inventors: Sergio Nicoletti, Sinard (FR); Mickael Brun, Eybens (FR); Serge Gidon, La Murette (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 0 days.

(21) Appl. No.: 14/576,794

(22) Filed: Dec. 19, 2014

(65) Prior Publication Data
US 2015/0192513 A1 Jul. 9, 2015

(30) Foreign Application Priority Data

Jan. 7, 2014 (FR) .................... 14 50069

(51) Int. Cl.
*G01N 21/00* (2006.01)
*G01N 21/3504* (2014.01)

(52) U.S. Cl.
CPC ...... *G01N 21/3504* (2013.01); *G01N 2201/061* (2013.01); *G01N 2201/066* (2013.01)

(58) Field of Classification Search
CPC . G01N 21/39; G01N 21/3504; G01N 21/031; G01N 2021/399; G01J 3/42
USPC ......................................... 356/437
See application file for complete search history.

(56) References Cited

U.S. PATENT DOCUMENTS

2007/0195319 A1* 8/2007 Kachanov et al. ............ 356/300
2007/0242720 A1 10/2007 Ecles et al.
2012/0267532 A1 10/2012 Udrea et al.

OTHER PUBLICATIONS

Barritault, Pierre, et al., "Mid-IR source based on a free-standing microhotplate for autonomous CO2 sensing in indoor applications", Sensors and Actuators A, Elsevier Sequoia, S.A., Lausanne, CH, vol. 172, No. 2, Sep. 21, 2011, pp. 379-385.
Barritault, Pierre, et al., "Low Power CO2 NDIR sensing using a micro-bolometer detector and a micro-hotplate IR-source", Sensors and Actuators B, Elsevier, vol. 182, Mar. 13, 2013, pp. 565-570.
Search Report issued in French Application No. 14/50069 on Oct. 24, 2014.

* cited by examiner

*Primary Examiner* — Tarifur Chowdhury
*Assistant Examiner* — Md Rahman
(74) *Attorney, Agent, or Firm* — Vedder Price, P.C.

(57) ABSTRACT

A gas detector including a planar mirror; a concave spherical mirror facing the planar mirror, having an optical axis orthogonal to the planar mirror, the distance between the planar and spherical being equal to 0.75 times the radius of curvature of the spherical mirror, to within 10%; a radiation emitter/receiver arranged at the point of intersection of the spherical mirror and of the optical axis; and a radiation receiver/emitter arranged at the point of intersection of the planar mirror and of the optical axis.

6 Claims, 5 Drawing Sheets

OPTICAL GAS DETECTOR

This application claims the priority benefit of French Patent application number 14/50069, filed on Jan. 7, 2014, the contents of which is hereby incorporated by reference in its entirety to the maximum extent allowable by law.

BACKGROUND

The present disclosure relates to an optical detector of the presence, and possibly of the content, of a gas in an atmosphere.

DISCUSSION OF THE RELATED ART

The use of optical detectors of the presence of a gas, for example, carbon dioxide, carbon monoxide, methane, or possibly various toxic gases such as xylene or toluene released by paints, is known. It should be noted that a detector of the presence of an excess of carbon dioxide and/or of carbon monoxide may form a fire detector.

Optical detectors which detect the presence of a gas by measuring the absorption of a light beam at one or a plurality of wavelengths corresponding to one or a plurality of absorption lines of the considered gas will here be considered. In such detectors, a radiation emitter generates an optical beam in a wavelength range comprising the wavelength of absorption lines characteristic of the gas to be detected. A radiation receiver following a filter at the wavelength of the absorption line to be detected indicates the absorption at this wavelength, and the presence and the content of the considered gas can be deduced therefrom. The filter(s) may correspond to an alternation of thin dielectric layers. They may also be an alternation of metallic and insulating strips with a step determining the filtering wavelength.

In order for the entire gas detection system to have a small bulk, it is often provided for the light beam propagating between the emitter and the receiver to travel one or a plurality of times back and forth via mirrors, generally curved mirrors.

Generally, existing gas detection systems implying at least one back and forth travel of a light beam between the radiation emitter and the radiation receiver have the disadvantage of being relatively delicate to manufacture. Indeed, the emitter, the receiver, and the mirrors require an accurate positioning with respect to one another.

SUMMARY

There thus is a need for an optical absorption gas detector which is particularly simple to manufacture.

It is also desired for this detector to be tolerant to mispositionings of the emitter, of the mirrors, and of the receiver with respect to one another.

Thus, an embodiment provides a gas detector comprising a planar mirror; a concave spherical mirror facing the planar mirror, having an optical axis orthogonal to the planar mirror, the distance between the planar and spherical mirrors being equal to 0.75 times the radius of curvature of the spherical mirror, to within 10%; a radiation emitter/receiver arranged at the point of intersection of the spherical mirror and of the optical axis; and a radiation receiver/emitter arranged at the point of intersection of the planar mirror and of the optical axis.

According to an embodiment, the planar mirror and the receiver/emitter form a single assembly comprising a support plate having a central portion comprising the receiver/emitter and having its remaining portion forming the planar mirror.

According to an embodiment, the planar mirror comprises a metallic reflective coating comprising at least two portions insulated from each other, each portion of the coating being in contact with a metal track connected to a terminal of the receiver/emitter.

According to an embodiment, the receiver/emitter is arranged on a membrane suspended above a central cavity of the support plate.

According to an embodiment, the gas detector further comprises at least one insulating layer comprising a central portion continued by arms connected to the rest of said at least one layer, the central portion of said at least one layer forming the membrane, the rest of said at least one layer being laid on the support plate.

According to an embodiment, the metal tracks are laid on the arms.

The foregoing and other features and advantages will be discussed in detail in the following non-limiting description of specific embodiments in connection with the accompanying drawings.

BRIEF DESCRIPTION OF THE DRAWINGS

For clarity, the same elements have been designated with the same reference numerals in the various drawings and, further, the various drawings are not to scale.

DETAILED DESCRIPTION

Figure 1:
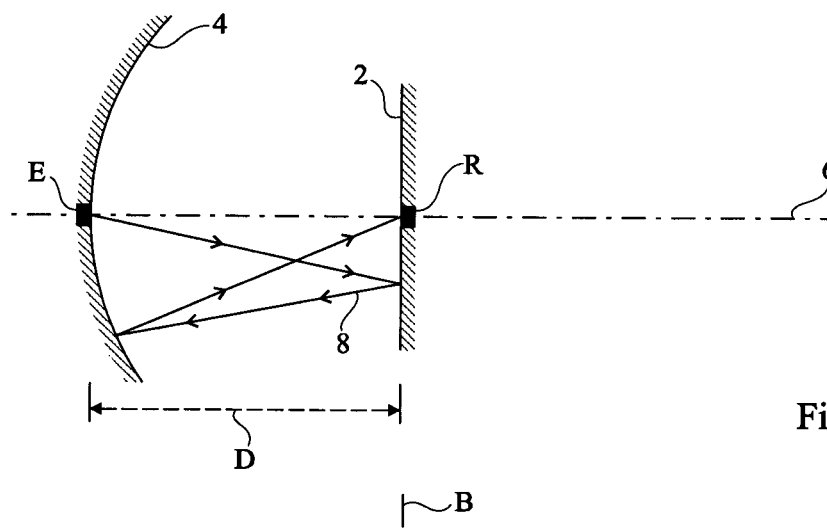
FIG. 1 is a simplified cross-section view of an embodiment of an optical gas detector.

FIG. 1 is a simplified cross-section view of an embodiment of an optical absorption gas detector.

The detector comprises a planar mirror 2 facing a concave spherical mirror 4 having a radius of curvature $R_C$, a radiation emitter E, and a radiation receiver R. Optical axis 6 of the system corresponds to the optical axis of spherical mirror 4 and is orthogonal to planar mirror 2.

Emitter E is arranged at the intersection of spherical mirror 4 with optical axis 6 and receiver R is arranged at the intersection of planar mirror 2 and of optical axis 6. Emitter E is preferably an emitter having a low directionality, or none at all (diverging emitter), facing planar mirror 2. Emitter E and receiver R are respectively connected to mirrors 2 and 4 by means, not shown in FIG. 1.

Mirrors 2 and 4 are arranged so that distance D separating the respective intersections of mirrors 2 and 4 with optical axis 6 is equal, to within 1%, or even to within 5%, or even to within 10%, to three quarters of radius of curvature $R_C$ of spherical mirror 4 ($D=0.75*R_C$). In such conditions, when a beam, a ray 8 of which has been shown, is emitted by emitter E, it is reflected by planar mirror 2 and then by spherical mirror 4 before reaching receiver R. The beam thus travels three times across the cavity. The system enlargement is equal to 0.5, that is, the image of the emitter on the receiver has a dimension which is half that of emitter E.

A gas detector comprising mirrors, such as the detector of FIG. 1, is well adapted to the detection of gas having absorption lines in infrared. The emitter may then be a filament heated to a temperature capable of emitting a sufficient quantity of radiation in a wavelength range including the absorption line to be detected, for example, a temperature in the range from 350° C. to 650° C. for a detection wavelength of 4.25 µm corresponding to an absorption line of carbon dioxide.

As an example, receiver R comprises a passive component (resistance) or an active component (diode or transistor) having characteristics which change according to their heating due to the reception of infrared rays. Thus, receiver R may be a bolometric or pyrometric sensor, or a thermoelectric cell.

Simulations have been performed by the inventors and show that such a system is little sensitive to misadjustments. As an example, when distance D between mirrors 2 and 4 is varied by 10%, the emitter image is enlarged and comes out of the receiver; the received energy then decreases by 10% only with respect to the energy received in the ideal case where the integrality of the emitter image occupies the receiver surface. When inclining by 0.05° or laterally displacing by 20 µm one or mirrors 2 or 4 relative to optical axis 6, the image of the emitter on the receiver is displaced and the energy received on the receiver only decreases by 10% with respect to the ideal case.

Such a positioning tolerance is particularly due to the fact that receiver R and emitter E respectively form one piece with mirror 2 and with mirror 4.

Further, due to the fact that one of the mirrors forming the optical system of the previously-described gas detector is a planar mirror rather than a curved mirror, the system is simpler to manufacture.

Figure 2A:
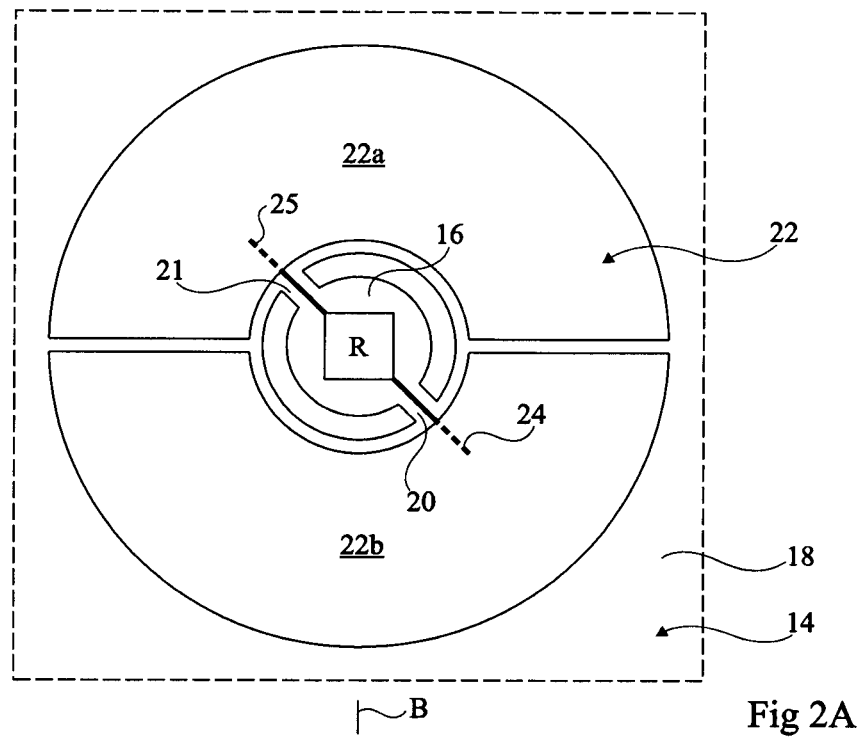
FIGS. 2A and 2B are simplified views of an embodiment of a planar mirror—receiver assembly.
Figure 2B:
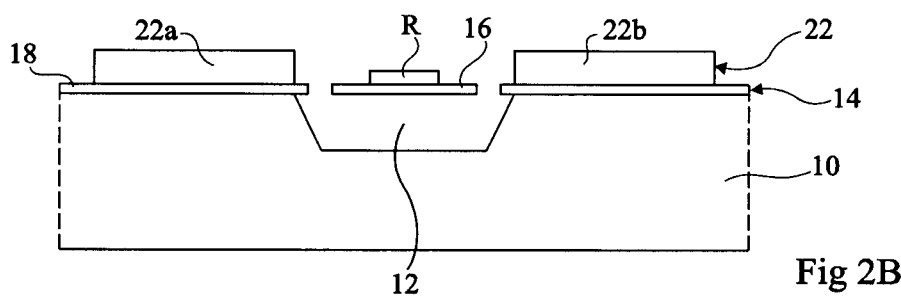

FIGS. 2A and 2B schematically show an embodiment of a planar mirror—receiver assembly, FIG. 2B being a cross-section view of FIG. 2A along cross-section plane BB. The assembly comprises:
- a support plate 10 provided with a cavity 12 on one of its surfaces;
- a layer or an assembly of layers 14, generally insulating, comprising a central portion 16, an external portion 18, and arms 20 and 21 interconnecting portions 16 and 18; portion 16 forms a membrane above cavity 12 and portion 18 coats support plate 10 around cavity 12;
- a reflective coating 22 coating the most part of portion 18 of layer 14; currently, the coating is metallic, for example, a gold layer;
- a receiver R solidly attached to membrane 16; and
- metal tracks 24 and 25 to connect the receiver.

In the shown example, reflective coating 22 has the shape of a disk divided into two half-disks 22a and 22b separated and insulated from each other. Metal tracks 24 and 25 are respectively laid on arm 20 and on arm 21. Metal tracks 25 and 24 extend from receiver R, respectively under portion 22a and under portion 22b of coating 22. Thus, coating 22, in addition to forming the reflective surface of planar mirror 2, is used to electrically connect receiver R, portions 22a and 22b forming electrodes.

Advantageously, the thermal loss at the level of receiver R are limited due to the fact that membrane 16 supporting the receiver is suspended above a cavity.

Receiver R and planar mirror 2 form an assembly enabling to suppress the step of assembling these two elements and to provide an accurate and stable positioning of receiver R relative to planar mirror 2.

FIGS. 3A to 6B are simplified views of an example of the central portion of a planar mirror—receiver assembly at different steps of an example of a manufacturing method.

Figure 3A:
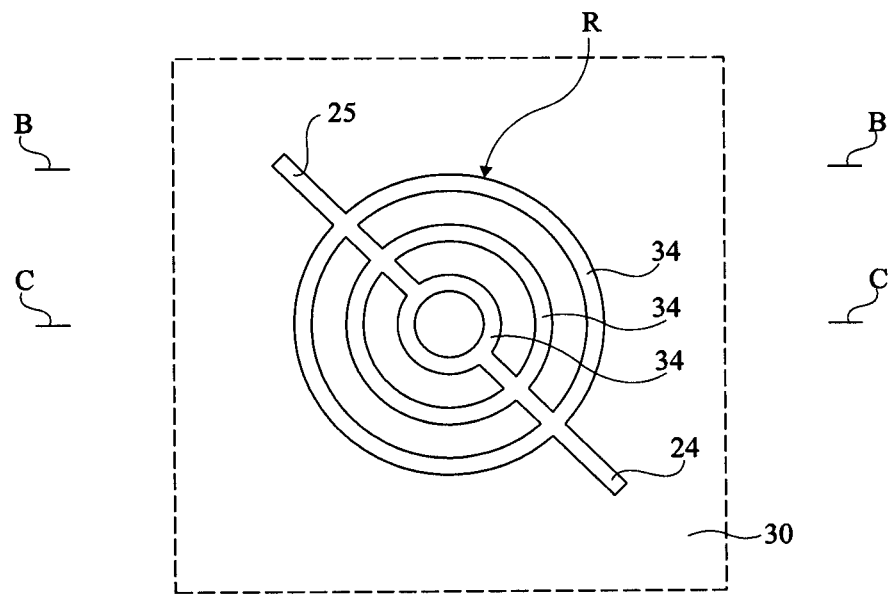
FIGS. 3A to 3C, 4A to 4C, 5A to 5C, and 6A and 6B are simplified views illustrating steps of a method of manufacturing a planar mirror—receiver assembly, FIGS. 3B and 3C, 4B and 4C, 5B and 5C, and 6B being cross-section views along planes BB and CC of the corresponding drawings bearing index A.
Figure 3B:
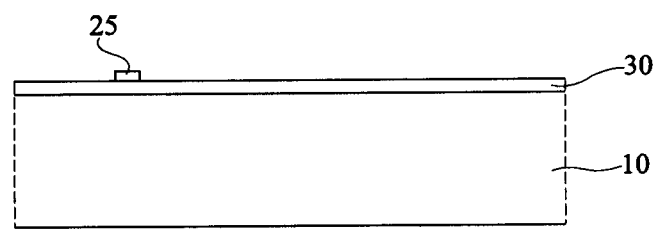
Figure 3C:
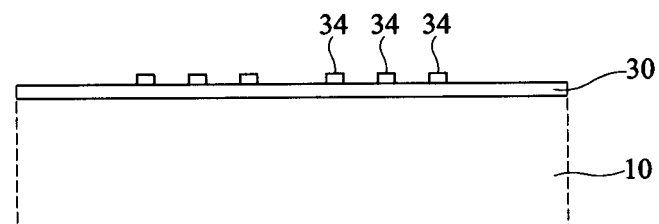

FIG. 3A is a simplified top view of the central portion of the planar mirror—receiver assembly after first steps, FIGS. 3B and 3C being cross-section views along planes BB and CC, respectively. These drawings show a support plate 10, for example, made of silicon, after a step of depositing an insulating layer 30, for example, made of $SiO_2$ or $Si_3N_4$, followed by a step of depositing a metal layer. The metal layer has been etched to form concentric metal rings 34 interconnected by rectilinear metal tracks 24 and 25 laid on insulating layer 30. Concentric rings 34 and metal tracks 24 and 25 altogether form a radiation receiver R. Metal rings 34 and metal tracks 24 and 25 are, for example, made of platinum or of titanium nitride. Thus, the voltage between tracks 24 and 25 depends on the resistance of the metal rings. This resistance depends on temperature and is an indication of the intensity of a radiation hitting metal rings 34.

Figure 4A:
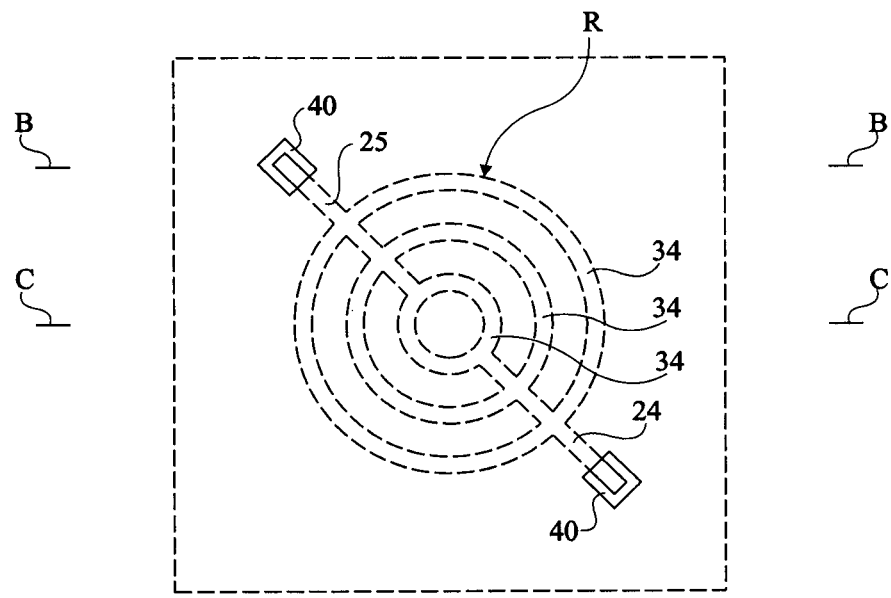
Figure 4B:
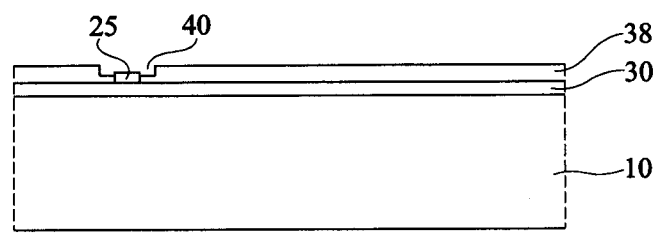
Figure 4C:
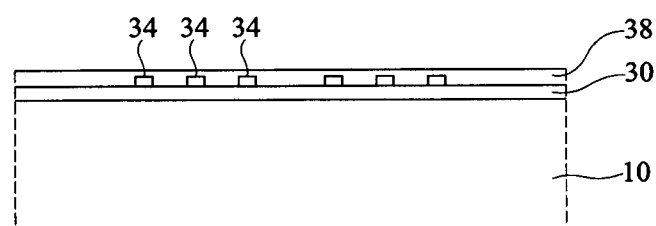

FIGS. 4B and 4C are cross-section views of FIG. 4A along planes BB and CC, respectively. FIGS. 4A to 4C schematically show the structure of FIGS. 3A to 3C after the successive steps of:
- depositing an insulating layer 38, for example, made of $SiO_2$ or $Si_3N_4$, and
- etching layer 38 to form openings 40 exposing the ends of metal tracks 24 and 25 of receiver R.

In FIG. 4A and in the following drawings, the portions of radiation receiver R covered with layer 38 are shown in dotted lines.

Figure 5A:
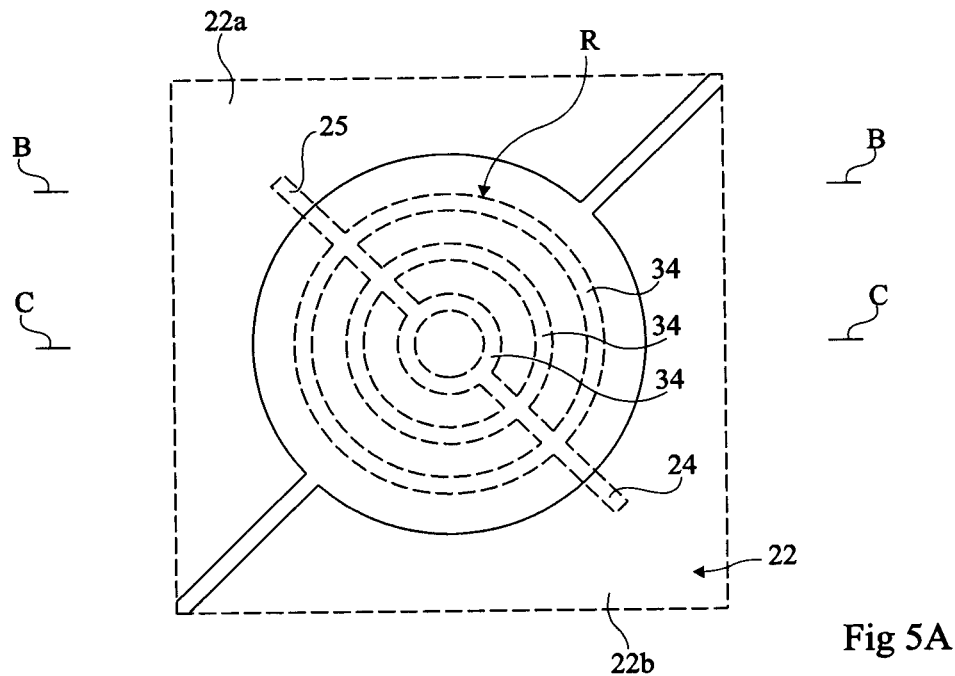
Figure 5B:
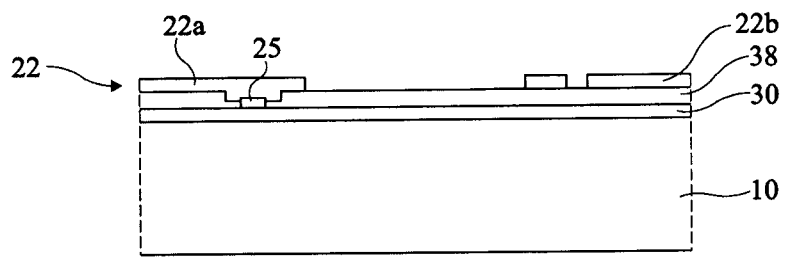
Figure 5C:
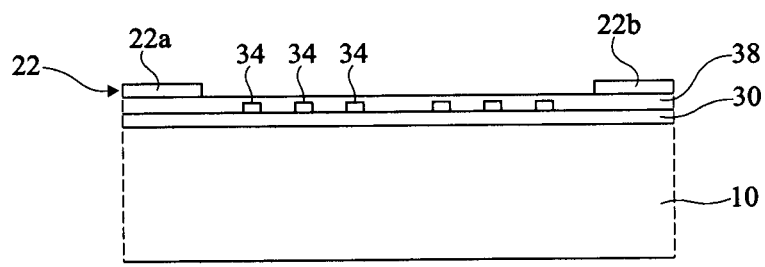

FIGS. 5B and 5C are cross-section views of FIG. 5A along planes BB and CC, respectively. FIGS. 5A to 5C schematically show the structure of FIGS. 4A to 4C after the successive steps of:
- depositing a reflective coating 22, and
- etching coating 22 to expose a central portion of layer 38 and to separate coating 22 in two portions 22a and 22b.

As previously indicated, coating 22 is preferably a metal layer, each of the two portions 22a and 22b of coating 22 being respectively connected to the end of track 25 and to the end of track 24 of receiver R to electrically connect the latter.

Figure 6A:
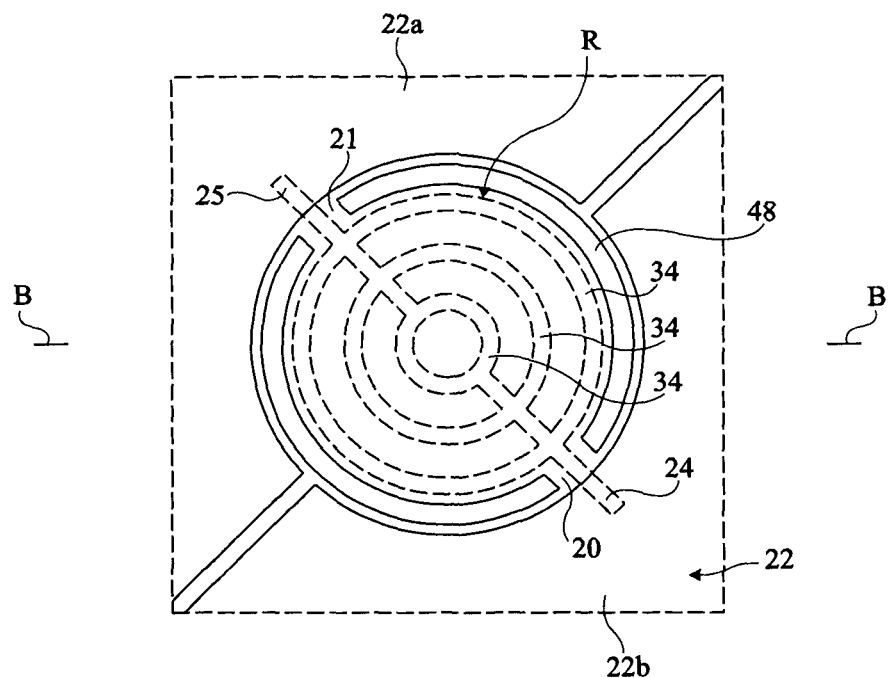
Figure 6B:
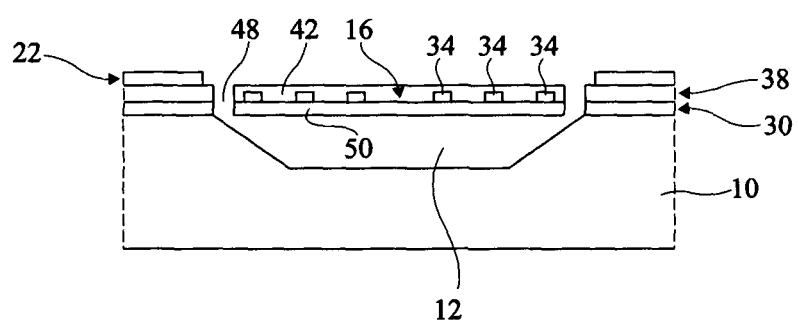

FIG. 6B is a cross-section view of FIG. 6A along plane BB. FIGS. 6A and 6B schematically show the structure of FIGS. 5A to 5C after the successive steps of:
- etching layers 30 and 38 to form an opening 48 around the assembly of rings 34 of receiver R,
- etching support plate 10 from opening 48 to form a central cavity 12 under a membrane 16 supporting receiver R.

The membrane is formed of a central portion 42 of layer 38 and of a central portion 50 of layer 30, central portion 50 being located opposite central portion 42. Central portions 42 and 50 are continued by arms 20 and 21 visible in FIG. 6A. Arms 20 and 21 support a portion of tracks 24 and 25, respectively. These arms connect central portions 50 and 42 of layers 30 and 38 to the rest of layers 30 and 38 resting on support plate 10. Arms 20 and 21 enable to maintain membrane 16 in place.

As an example, if it is desired for the optical path between the emitter and the receiver to be 8 cm, distance D between mirrors 2 and 4 will be equal to approximately one third of this value, that is, D=2.67 cm. The dimensions of emitter E, of receiver R, and of mirrors 2 and 4 will be selected by those skilled in the art according to the desired bulk as well as according to the desired detector performance. For example, an emitter diameter equal to 150 µm and a receiver diameter equal to 75 µm may be selected. Diameters equal to 0.45 cm and 0.9 cm may also respectively be selected for the planar and spherical mirrors. The gas sensor thus obtained is very compact.

Specific embodiments have been described. Various alterations, modifications, and improvements will readily occur to those skilled in the art.

The receiver may be divided into a plurality of elementary receivers, each being associated with a specific filter. The different elementary receivers enable to provide a reference indication and/or to detect a plurality of different gases. The reference is especially used to take into account environmental fluctuations and/or intensity fluctuations in the emitter.

It will be within the abilities of those skilled in the art to modify the order of the steps and/or add or suppress steps in the previously-described manufacturing method.

Although a gas detector having its emitter E forming one piece with spherical mirror 4 and having its receiver R forming one piece with planar mirror 2 has been described, due to the law of reflection, it is possible to exchange the positions of emitter E and of receiver R. Receiver R is then arranged at the level of spherical mirror 4, emitter E being arranged on planar mirror 2. In this case, the system enlargement is equal to 2. It will be chosen to arrange the emitter or the receiver on the side of the spherical mirror and to arrange the receiver or the emitter on the side of the planar mirror according to specific manufacturing imperatives. This choice will also be dictated by dimensional constraints. Indeed, the device (receiver or emitter) arranged at the level of the planar mirror is twice smaller than the device at the level of the spherical mirror.

Finally, although a gas detector where the receiver is maintained by a membrane above a cavity has been described, it should be noted by those skilled in the art that, according to the type of emitter or receiver selected, such a cavity may be of no use.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:
1. A gas detector comprising:
a planar mirror (2);
a concave spherical mirror (4) facing the planar mirror (2), having an optical axis (6) orthogonal to the planar mirror, the distance (D) between the planar and spherical mirrors being equal to 0.75 times the radius of curvature of the spherical mirror, to within 10%;
a radiation emitter (E); and
a radiation receiver (R),
wherein a first element selected from the radiation emitter (E) and the radiation receiver (R) is arranged at the point of intersection of the spherical mirror (4) and of the optical axis (6),
wherein a second element selected from the radiation receiver (R) and the radiation emitter (E) is arranged at the point of intersection of the planar mirror (2) and of the optical axis (6), and
wherein radiation emitted by the radiation emitter (E), reflected between the spherical mirror (4) and planar mirror (2) and received by the radiation receiver (R) permits detection of a gas through which the radiation propagates.

2. The detector of claim 1, wherein the planar mirror (2) and the radiation emitter (E) or the radiation receiver (R) form a single assembly comprising a support plate (10) having a central portion comprising the second element and having its remaining portion forming the planar mirror (2).

3. The detector of claim 2, wherein the planar mirror (2) comprises a metallic reflective coating (22) comprising at least two portions (22a, 22b) insulated from each other, each portion of the coating being in contact with a metal track (24, 25) connected to a terminal of the second element.

4. The detector of claim 2, wherein the second element is arranged on a membrane (16) suspended above a central cavity (12) of the support plate (10).

5. The detector of claim 4, further comprising at least one insulating layer (14; 30, 38) comprising a central portion (16; 42, 50) continued by arms (20, 21) connected to the rest of said at least one layer, the central portion of said at least one layer forming the membrane (16), the rest of said at least one layer being laid on the support plate (10).

6. The detector of claim 5, wherein the metal tracks (24, 25) rest on arms (20, 21).

* * * * *